United States Patent [19]

Picart

[11] 4,432,973
[45] Feb. 21, 1984

[54] BENZOYL- AND α-HYDROXYBENZYL-PHENYL-GLYCOSIDES AND APPLICATION THEREOF IN THERAPEUTICS

[75] Inventor: François Picart, Dijon, France

[73] Assignee: Societe de Recherches Industrielles (S.O.R.I.), Paris, France

[21] Appl. No.: 314,032

[22] Filed: Oct. 22, 1981

[30] Foreign Application Priority Data

Oct. 29, 1980 [FR] France ............................. 80 23133

[51] Int. Cl.³ ..................... A61K 31/70; C07H 15/20
[52] U.S. Cl. ................................... 424/180; 536/4.1; 536/17.9; 536/17.6; 536/17.8
[58] Field of Search ................... 424/180; 536/4, 18, 536/4.1, 17.6, 17.8, 17.9

[56] References Cited

U.S. PATENT DOCUMENTS

| | | | |
|---|---|---|---|
| 2,218,569 | 10/1940 | White | 536/4 |
| 2,798,079 | 7/1957 | Linn | 536/4 |
| 3,152,115 | 10/1964 | Morel et al. | 536/4 |
| 3,356,674 | 12/1967 | Ikeda et al. | 536/4 |
| 3,496,196 | 2/1970 | Suami et al. | 536/4 |
| 3,960,835 | 6/1976 | Robertson | 536/4 |

Primary Examiner—Johnnie R. Brown
Attorney, Agent, or Firm—Schwartz, Jeffery, Schwaab, Mack, Blumenthal & Koch

[57] ABSTRACT

The present invention relates to the benzoyl- and α-hydroxybenzyl-phenyl-oside derivatives of general formula:

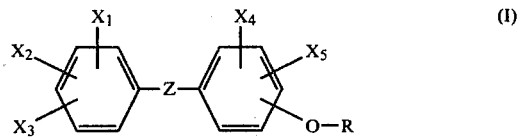

[in which Z is CO or CHOH, $X_1$, $X_2$, $X_3$, $X_4$ and $X_5$, which are identical or different, each represent an atom of hydrogen, an atom of halogen, an alkyl group with 1 to 4 carbon atoms, an alkyl group with 1 to 4 carbon atoms substituted by one or more atoms of halogen, an OH group, an alkoxy group with 1 to 4 carbon atoms, an alkoxy group with 1 to 4 carbon atoms, substituted by one or more atoms of halogen, a nitro group, a cyano group, a thiocyano group, an isothiocyano group, a NR'R" group (where R' and R", identical or different, each represent an atom of hydrogen or an alkyl group with 1 to 4 carbon atoms) $X_1$ being able, in addition, to represent an —NH—CS—O—$CH_3$ group or an —O—C($CH_3$)$_2$ $CO_2$—R''' group (where R''' is an alkyl group with 1 to 4 carbon atoms and, preferably, an isopropyl group); and R represents a radical ose (the hydroxyl and amine functions of the radical ose being able to be substituted by acyl, alkyl or sulfate groups)], and to their diastereoisomers. It also relates to the method for preparing these derivatives and to their application in therapeutics.

11 Claims, No Drawings

BENZOYL- AND α-HYDROXYBENZYL-PHENYL-GLYCOSIDES AND APPLICATION THEREOF IN THERAPEUTICS

The present invention relates, as new industrial products, to the derivatives of benzoyl-phenyl-osides and of α-hydroxybenzyl-phenyl-osides of formula (I) hereinbelow. It also relates to their method of preparation and to their application in therapeutics, particularly as anti-ulcerous agents, platelet anti-aggregant agents, anti-thrombotic agents and cerebral oxygenators.

In the past, it has been proposed to use phenylglycosides as agents possessing antiviral properties, cf. to this end the article by Hitoshi Arita, Carbohydrate Research 62, 143-154 (1978).

It has now been surprizingly found that compounds which are structurally different since they present in particular an additional benzoyl or α-hydroxybenzyl group with respect to the phenyl-glycosides, are particularly advantageous in the treatment of ulcers and illnesses connected with circulatory disorders, and particularly in the treatment of cerebral senescence.

The compounds according to the invention are characterised in that they are selected from the group constituted by:

(i) the compounds of general formula:

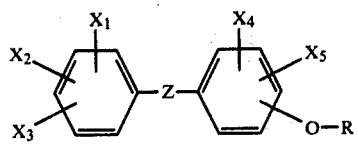

in which:

Z represents >CO or >CHOH;

$X_2$, $X_3$, $X_4$ and $X_5$, which are identical or different, each represent an atom of hydrogen, an atom of halogen, an alkyl group with 1 to 4 carbon atoms, an alkyl group with 1 to 4 carbon atoms substituted by one or more halogen atoms (particularly a $CF_3$ group), an OH group, an alkoxy group with 1 to 4 carbon atoms, an alkoxy group with 1 to 4 carbon atoms substituted by one or more halogen atoms, a nitro group, a cyano group, a thiocyano group, an isothiocyano group, a NR'R" group (where R' or R", which are identical or different, each represent an atom of hydrogen or an alkyl group with 1 to 4 carbon atoms);

$X_1$ represents an atom of hydrogen, an atom of halogen, an alkyl group having 1 to 4 carbon atoms, an alkyl group having 1 to 4 carbon atoms substituted by one or more halogen atoms (particularly a $CF_3$ group), an OH group, an alkoxy group with 1 to 4 carbon atoms, an alkoxy group having 1 to 4 carbon atoms substituted by one or more atoms of halogen, a nitro group, a cyano group, a thiocyano group, an isothiocyano group, a NR'R" group (where R' and R" which are identical or different, each represent an atom of hydrogen or an alkyl group with 1 to 4 carbon atoms), an $-NH-C-S-O-CH_3$ group or an $-O-C(CH_3)_2CO_2-R'''$ group (where R''' is an alkyl group with 1 to 4 carbon atoms, and preferably an isopropyl group);

R represents a radical ose, possibly substituted, and (ii) their diastereoisomers when Z is CHOH.

The invention also includes the acid addition salts of the compounds of formula (I) when at least one of the groups $X_1$, $X_2$, $X_3$, $X_4$, $X_5$ and R comprises a basic group.

The group —O—R, taking into account the structure of formula (I) given hereinabove, may be in ortho, meta or para position with respect to the group Z.

The term "ose" in the definition of the radical R here denotes any elementary glucidic, non-hydrolysable unit of empirical formula $(CH_2O)_n$. According to the invention, each hydroxyl function of the ose radical may be acylated (particularly by $COCH_3$), alkylated (particularly by $CH_3$ or $CH_2C_6H_5$) or sulfated (particularly by $SO_3NH_4$, $SO_3Na$ or $SO_3K$), and the hydroxyl function of the carbon atom in 2 position may be replaced by an amine function, itself capable of being acylated (particularly by $COCH_3$), alkylated (particularly by $CH_3$ or $CH_2C_6H_5$) or sulfated (particularly by $SO_3NH_4$, $SO_3Na$ or $SO_3K$).

Consequently, R represents in particular a glycosyl radical such as β-D-glucosyl, β-D-xylosyl, β-D-galactosyl, β-D-glucosaminyl or α-L-rhamnosyl, the hydroxyl and amine functions being able, if need be, to be substituted by acyl, alkyl or sulfate groups.

When $X_1$ represents an $-NH-CS-O-CH_3$ or $-O-C(CH_3)_2CO_2-R'''$ group, such a group is advantageously in para position with respect to the group Z and, in this case, each of the groups $X_2$, $X_3$, $X_4$ and $X_5$ represents an atom of hydrogen.

Atom of halogen is understood here to mean the atom of fluorine, chlorine, bromine and iodine, the preferred halogens being fluorine, chlorine and bromine and among these latter, the most advantageous halogens from the therapeutic point of view are chlorine and bromine.

Taking into account the above definitions, the invention therefore covers the carbonyl derivatives (Z=CO) of the benzoyl-phenyl-oside type and the carbinol derivatives (Z=CHOH) of the α-hydroxybenzyl-phenyl-oside type.

Among the compounds of formula (I) which are preferred according to the invention, particular mention may be made of the oside derivatives where Z is CO or CHOH; $X_1$, $X_2$, $X_3$, $X_4$ and $X_5$, which are identical or different, each represent H, Cl, Br, $CH_3$, $CF_3$, OH, $OCH_3$, $NO_2$, $NH_2$, $N(CH_3)_2$, NCS, $X_1$ also representing in para position with respect to the group Z, an $-OC(CH_3)_2CO_2-CH(CH_3)_2$ group or an $-NH-C-S-OCH_3$ group when $X_2=X_3=X_4=X_5=H$; and R represents an ose radical such as β-D-glucosyl, β-D-xylosyl, β-D-galactosyl, α-L-rhamnosyl, β-D-glucosaminyl, the atom of hydrogen of the OH groups of the oside radical being able, if need be, to be replaced by a $COCH_3$, $CH_3$, $CH_2C_6H_5$, $SO_3NH_4$, $SO_3Na$, $SO_3K$ radical and the amine function of the oside group being able to be substituted by a $COCH_3$ group.

The compounds of formula (I) may be prepared according to a method known per se according to a conventional reactional mechanism. Thus, a phenyl-phenol of formula:

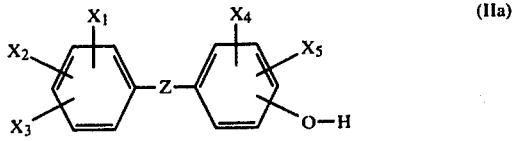

(where Z, $X_1$, $X_2$, $X_3$, $X_4$ and $X_5$ are defined as hereinabove) is subjected to osidation according to the method of Koenig-Knorr [described in the work "The Carbohydrates, Chemistry and Biochemistry" (2nd edition, Academic Press, New York and London 1972) Vol. IA, pages 295-301] by condensation of a phenol (IIa) with a haloacyloside in the presence of a catalyst such as mercuric cyanide, $Ag_2O$, $AgCO_3$, $CdCO_3$ or of a tertiary amine such as collidine;

the method of Helferich (ibidem, pages 292-294) by condensation of an acyloside with a phenol (IIa) in the presence of a Lewis acid; or the so-called ortho-ester method (ibidem, pages 300-304).

The preferred method which is recommended is characterised in that:

(i) a derivative of phenyl-phenol of formula:

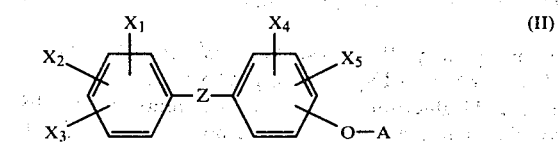

(where Z, $X_1$, $X_2$, $X_3$, $X_4$ and $X_5$ are defined as indicated hereinabove and A represents H or, preferably Na, K) is reacted with an ose derivative selected from the group constituted by haloacyloses and acyloses, in an inert solvent, at a rate of 1 mole of (II) for 1.1 to 1.2 mole of (ii) if necessary, a de-acetylation reaction is carried out by heating to reflux in a lower alcohol with 1 to 4 carbon atoms (preferably methanol) in the presence of a metallic alcoholate, preferably magnesium methylate or sodium methylate.

According to a preferred embodiment of the method which is recommended, 1 mole of derivative of phenyl-phenol (II) (where A is Na or K) is reacted at stage (i) with 1.1 to 1.2 mole of a haloacylose of formula:

(where Hal is an atom of halogen F, Cl, Br, I, and preferably Cl or Br to have an optimal yield, and R represents a radical ose where the OH and $NH_2$ functions are protected, preferably, by an acyl group), in an inert solvent selected from the polar or apolar solvents (such as in particular dimethylformamide, tetrahydrofuran, dioxan, methanol, ethanol, acetonitrile, nitromethane, dimethylsulfoxide and mixtures thereof with one another or with the haloalkanes, in particular the mixtures $DMF-CH_2Cl_2$, $DMF-CHCl_3$, $DMF-ClCH_2CH_2Cl$). Acetonitrile will advantageously be used as solvent, the reaction of (II) with (III) being effected at a temperature of between 0° C. and the reflux temperature of the medium (advantageously between 0° C. and 25° C. and particularly at ambient temperature) for 10 to 40 minutes (advantageously 10 to 20 minutes for the "carbonyl" compounds Z=CO, and 20 to 30 minutes for the "carbinol" compounds Z=CHOH). The derivative obtained according to this technique is subjected, if need be, to a de-acylation reaction.

When A represents H, it is recommended to use a catalyst such as mentioned hereinabove, particularly $Ag_2O$.

In addition to this process which is suitable for the synthesis of compounds I of the "carbonyl" type and of the "carbinol" type, another method may be carried out for obtaining the compounds of the "carbinol" type by reduction of the corresponding "carbonyl" derivative.

This reduction reaction is carried out by reacting a compound of formula I where Z=CO with an agent selected from the group constituted by complex metallic hydrides such as $LiAlH_4$ and $KBH_4$, in an inert solvent such as ether, tetrahydrofuran and the lower alcohols, particularly methanol and ethanol, at a temperature of between 0° C. and 50° C. (preferably between 0° C. and 25° C., and in particular at ambient temperature).

The compounds of formula I where Z is CHOH may be divided into their 2 diastereoisomers according to a method known per se, particularly by fractional recrystallisation. The resolution of the mixture of the diastereoisomers may advantageously be effected (a) by dissolution of said mixture in $CH_3OH-H_2O$ (1:1) v/v and recrystallisation up to constant rotatory power in $CH_3OH-H_2O$ (1:1) v/v, to obtain the dextrorotatory substance, then (b) by taking up the recrystallisation filtrates in $CH_3OH-H_2O$ (1:2) v/v and recrystallisation up to constant rotatory power in $CH_3OH-H_2O$ (1:2) v/v, to obtain the laevorotatory substance.

According to the invention, a therapeutic composition is proposed, characterised in that it contains, in association with a physiologically acceptable excipient, at least one compound selected from the group constituted by the products of formula I, their diastereoisomers and their non-toxic salts.

The compounds of formula (I) are useful in therapeutics as anti-ulcerous agents, platelet anti-aggregant agents, atithrombotic agents or cerebral oxygenators. The compounds most interesting in therapeutics are the products of Example 1 (Code No. 163), 97 (Code No. 265), 98 (Code No. 390) and 99 (Code No. 391) which are particularly indicated as veinous antithrombotic agents, the preferred compound being the product of Example 97.

Other features and advantages of the invention will be more readily understood on reading the following examples of preparation which have been given by way of non-limiting illustration.

Preparation I

Obtaining of [4-(4-nitrobenzoyl)-phenyl]-2,3,4-tri-(O-acetyl)-β-D-xylopyranoside (Code No. 236; Example 41)

In a 500 ml flask is suspended the dry phenate obtained by action of 4.1 g of sodium hydroxide on 25 g of 4'-paranitro-benzoyl-phenol in a mixture of 65 ml of DMF and 200 ml of dichloro-1,2-ethane.

The mixture is taken to reflux and 45 g of 2,3,4-tri-(O-acetyl)-1-bromo-α-D-xylopyranose are added quickly. The mixture is then heated for 3 hours at reflux. After hydrolysis, it is extracted with ethyl acetate and the organic phase is washed with sodium hydroxide at 40 g/l. It is evaporated to dryness and a yellow oil is obtained which crystallises in anhydrous ether. Finally, the mixture is recrystallised in methanol. 22 g of the expected product are thus obtained.

m.p.=150° C., $\alpha_D^{20°~C.}=-33.3°$ (c=0.9 g/l;$ClCH_2CH_2Cl$).

Preparation II

Obtaining of [4-(4-nitrobenzoyl)-phenyl]-β-D-xylopyranoside Code No. 163; Example 1)

20 g of acetylated product obtained according to Preparation I are dissolved hot in 300 ml of methanol and 2 g of Mg(OCH$_3$)$_2$. The mixture is taken to reflux for 2 hours. 1 liter of methanols is then added and the mixture is reheated up to complete dissolution. The yellow solution obtained is filtered. After evaporation of the solvent, the expected product is obtained with a yield of 90%.

m.p.=200° C., $\alpha_D^{20°\ C.}=-26.6°$ (c=0.6 g/l; methanol).

Preparation III

Obtaining of [4-(4-nitrobenzoyl)-phenyl]-2-(N-acetyl)-β-D-glucosaminide (Code No. 207; Example 44)

In a 500 ml flask is suspended the dry phenate obtained by action of 0.540 g of NaH on 5 g of 4'-paranitrobenzoylphenol, in a mixture of 25 ml of DMF and 25 ml of dichloroethane. 8.3 g of acetochloroglucosamine are added to the reaction medium and the mixture is stirred for 3 hours at 40° C. After hydrolysis, it is extracted with ethyl acetate, washed in sodium hydroxide at 40 g/l and finally with water.

After evaporation of the solvent, an oil is obtained which precipitates in ether. The acetylated derivative obtained is recrystallised in ethyl acetate. (Yield=59%; m.p.=238° C.).

This acetylated derivative is suspended in 150 ml of methanol with 0.150 g of sodium methylate. The reaction medium is stirred for 2 hours at ambient temperature then is hydrolysed on ice. After filtration, washing with water and recrystallisation in methanol, 4.4 g (yield=80%) of the expected product are obtained.

m.p.=204° C., $\alpha_D^{20°\ C.}=+12.5°$ (c:0.6 g/l, methanol).

Preparation IV

Obtaining of [3-(4-trifluoromethylbenzoyl)-phenyl]-β-D-xylopyranoside (Code No. 428; Example 53)

In a 250 ml flask, the following are added in order: 9.4 g of 3-(paratrifluoromethylbenzoyl)-phenol, 15 g of acetobromoxylose, the quantity of dry silver oxide (freshly prepared by action of sodium hydroxide at 40 g/l on 14 g of silver nitrate) and 100 ml of acetonitrile. The mixture is stirred for 10-20 mins. in a nitrogen atmosphere and away from the light.

After filtration then hydrolysis, the mixture is extracted with ethyl acetate, washed with sodium hydroxide at 40 g/l then with water. After evaporation of the solvent, the mixture is recrystallised in the (1:1) v/v methanol-water mixture. 10 g (yield: 55%) of the acetylated derivative are thus obtained (m.p.=90° C.) which is taken up in 100 ml of methanol with 0.1 g of sodium methylate. The mixture is stirred for 1 hour then passed over Amberlite IR 120 H resin, filtered, then the solvent is evaporated. After recrystallisation in methanol, 5 g (yield=65%) of the expected product are obtained.

m.p.=120° C. $\alpha_D^{20°\ C.}=-38°$ (c=0.5 g/l; methanol).

Preparation V

Obtaining of [4-(4-chlorobenzoyl)-phenyl]-3,4,6-tri-(ammonium-sulfate)-2-N-acetyl-β-D-glucosaminide (Code No. 358; Example 67)

In a nitrogen atmosphere and at −10° C., 15 g of [4-(parachlorobenzoyl)-phenyl]-2-N-acetyl-β-D-glucosaminide, 29.6 ml of pyridine and 150 ml of DMF are mixed. 12.3 ml of sulfonyl chloride are added drop by drop. After stirring of the reaction medium at ambient temperature (15°-25° C.) for 12 hours, the solution is taken to pH 9 by addition of sodium bicarbonate. After extraction with ethyl acetate, the aqueous phase is evaporated at 35° C. maximum. The product is then taken up in 400 ml of water and is filtered. The filtrate is passed three times over OC1031 resin. The alcoholic phases are then evaporated. The residue is taken up in (40:12:10:1) v/v butanol-ethanol-water-ammonia-mixture and the solution passed over a neutral alumina column. After evaporation of the solvent, 16.5 g of the expected product are obtained.

m.p.=200° C. (with decomposition), $\alpha_D^{20°\ C.}=-2.1°$ (c=2.6 g/l; water).

Preparation VI

Obtaining of [4-(4-nitro-α-hydroxybenzyl)-phenyl]-β-D-xylopyranoside (Code No. 265; Example 97)

10 g (26.6 millimoles) of [4-(4-nitrobenzoyl)-phenyl]-β-D-xylopyranoside (Code No. 163; Example 1; cf. Preparation II) are suspended in 200 ml of methanol then 1.56 g (26.6 millimoles) of KBH$_4$ is added. The reaction medium thus obtained is stirred for 2 hours at ambient temperature (15°-25° C.). The progress of the reaction of reduction is controlled by CCM [solvent: toluenemethanol (3:1) v/v]. After evaporation in vacuo of the methanol, the product is taken up in ethyl acetate then washed with water (3×50 ml). It is dried over magnesium sulfate then, after evaporation of the solvent, it is recrystallised in the (3:7) v/v methanol-water mixture. 6.5 g (yield=65%) of the expected product are obtained.

m.p.=142° C., $\alpha_D^{20°\ C.}=-17°$ (c=0.5 g/l:methanol).

Preparation VII

Obtaining of [4-(4-nitro-α-hydroxybenzyl)-phenyl]-2,3,4-tri-(O-acetyl)-β-D-xylopyranoside (Example 96)

In a flask protected from the light and provided with a CaCl$_2$ tube, 2.45 g of 4-(4-nitro-α-hydroxy-benzyl)-phenol, 3.4 g of acetobromoxylose, 2.4 g of freshly prepared silver oxide and 200 ml of acetonitrile are placed. It is stirred for half an hour at ambient temperature, then filtered on fritted glass. After hydrolysis of the filtrate, the product is extracted with ethyl acetate then washed with water. The organic phase is dried, filtered then the solvent is evaporated. An oil is obtained which is purified over a silica column [eluent: (4:1) v/v toluene-ethyl acetate]. 2 g of expected product are thus obtained (yield=40%).

m.p.=80° C., $\alpha_D^{20°\ C.}=-25°$ (c=0.5 g/l; methanol).

Preparation VIII

By de-acylating the product obtained according to Preparation VII, by heating to reflux in CH$_3$OH in the presence of magnesium methylate, the [4-(4-nitro-α-hydroxy-benzyl)-phenyl]-β-D-xylopyranoside (according to Preparation VI above) is obtained.

Preparation IX

Separation of the dextrorotatory diastereoisomer (Code No. 390; Example 98) and laevorotatory diastereoisomer (Code No. 391; Example 99) of [4-(4-nitro-α-hydroxybenzyl)-phenyl]-β-D-xylopyranoside 40 g of the product of Example 97 (Code No. 265) are dissolved in 400 ml of the (1:1) v/v methanol-water mixture and the solution is recrystallised up to constant rotatory power. 16 g of the dextrorotatory diastereoisomer are obtained.

m.p. = 162° C., $\alpha_D^{20°\ C.} = +21°$ (c=0.48 g/l; methanol).

The filtrates of the preceding recrystallisation operations are taken up in 300 ml of the (1:2) v/v methanol-water mixture and the product is recrystallised up to constant rotatory power. 15 g of the laevorotatory diastereoisomer are obtained.

m.p. = 158° C., $\alpha_D^{20°\ C.} = -50°$ (c=0.48 g/l; methanol).

Preparation X

Obtaining of [2-(4-nitrobenzoyl)-phenyl]-2,3,4-tri-(O-acetyl)-β-D-xylopyranoside (Example 141)

In a 100 ml flask, 120 mg of NaH and 10 cm³ of DMSO are introduced. After 15 minutes, $2\times10^{-3}$ mole (486 mg) of 2'-paranitrobenzylphenol then $4\times10^{-3}$ mole (1.3 g) of acetobromoxylose and 5 ml of DMSO are added. The mixture is stirred for 1 hour at ambient temperature (15°-20° C.). It is extracted with ether and the ethereal phase is washed with water. After evaporation of the ether, 1.57 g of the expected crude product is obtained which is chromatographed over silica column [eluent: (4:1) v/v toluene-ethyl acetate] to collect 400 mg of expected pure product (yield: 40%).

m.p. 142° C.

Preparation XI

Obtaining of [2-(4-nitrobenzoyl)-phenyl]-β-D-xylopyranoside (Example 57)

According to the modus operandi described in Preparation II hereinabove, and from 50 mg of [2-(4-nitrobenzoyl)-phenyl]-2,3,4-tri-(O-acetyl)-β-D-xylopyranoside obtained according to Preparation X, the expected product is obtained with a yield of 90%.

m.p. 164° C.

A certain number of compounds of formula (I) has been shown in non-limiting manner in Table I hereinbelow (where the position of the substituents has been given arbitrarily, the numbering of the vertices of the phenyl rings being made from the central group Z). Table II hereinbelow also shows the physical properties of part of these compounds, namely the melting point (m.p.) and the rotatory power ($\alpha_D^{20°\ C.}$); for the latter, the nature of the solvent and the concentration (in g/l) have been specified.

Tables III to VII hereinbelow summarise the results of the tests (toxicity, anti-ulcerous, platelet anti-aggregant, antithrombotic and anti-hypoxic activities) undertaken on a certain number of products according to the invention. The modi operandi carried out are as follows:

Acute toxicity

The acute toxicity was studied in the mouse by the I.P. route. It is expressed in the form of DL-50 (lethal dose involving the death of half of the animals) or DL-0 (maximum non-lethal dose). The results are given in Table III.

Spontaneous aggregation

The technique used is that of Sanders described in Laboratory Animal Science 27 (No. 5), pages 757–761 (1977).

After administration at 100 mg/kg I.P. (unless specified to the contrary in Table V hereinbelow) of the product to be tested to adult male reproducing rats, two blood samples are taken, one on sodium citrate and the other on sodium citrate treated with formaldehyde at instant t=5 hours.

After centrifugation of the samples, a platelet count is made on the supernatant liquid. The spontaneous aggregation index according to Wu and Hook Stroke 6, 521-524 (1975) is expressed by the relation:

$$I = \frac{\text{Number of platelets after fixation with formaldehyde}}{\text{Number of circulating platelets}}$$

The results relative to the percentage of the inhibition of the platelet aggregation are given in Table V.

Veinous thrombosis

The technique used is similar to the one described by Peterson-Zucker in Thrombo.Diath.Haemorh. 23, 1, (1970).

An occlusive thrombus is created in the interior vena cava of a rat by the combined action of an endothelial alteration and a veinous stasis for 15 mins. and 4 to 5 hours after administration of the product to be tested (100 mg/kg I.P.). The results are shown in Table VI hereinbelow.

Ulcer caused by aspirin

The experiment is carried out on male Wistar rats of 180 to 200 g. The products to be tested are administered at 100 mg/kg I.P. (unless indicated to the contrary in Table IV).

At t=0, the rats are made to fast and a first administration of the product to be tested is made.

At t=18 hours, 2 ml of an ulcer-forming suspension with 192 mg of aspirin/kg are administered per os then a second administration of the product to be tested is made.

At t=22 hours, the animals are sacrificed and the ulcers are marked as follows:

small point-like ulcers: mark 1
more extensive ulcers: mark 3
highly extensive or very deep ulcers: mark 9

This marking is standardised with respect to a control batch and to cimetidine (a reference product) to which index 1 has been allocated.

Hypoxia

The experiment is carried out on batches of 20 Swiss male mice weighing from 20 to 30 g. Each product to be tested is administered to the mice by intraperitoneal route at a dose corresponding to 1/10th of the LD-50 or at a dose of 100 mg/kg when the LD-0 is higher than or equal to 800 mg/kg. The mice are placed in a nitrogenoxygen (95:5) v/v atmosphere. The survival time of the mice is then measured up to 15 minutes maximum.

The results shown in Table VII are expressed in percentage of survival with respect to a non-treated control batch and a batch treated with an anti-hypoxic reference product [specialty known under the trade name of "Duxil" and which is constituted by a mixture of Almitrine bis-methanesulfonate and of Raubasine in the weight ratio 3:1], the anti-hypoxic reference product being administered at the dose of 18 mg/kg I.P.

The results concerning the anti-ulcerous activity of the products of formula I are shown in Table IV hereinbelow.

The products of formula (I) may be administered, particularly by the oral route, in the form of capsules or tablets which are sugar-coated or not, each containing 0.05 to 1 g of at least one compound of formula (I) as active ingredient, and preferably 0.1 to 0.5 g, on the one hand, and by the injectable route, in the form of solutions containing from 0.05 to 0.3 g of active ingredient in 2 to 10 $cm^3$ of distilled water, on the other hand. These galenic forms may be administered at a rate of 1 to 3 times per day.

TABLE I

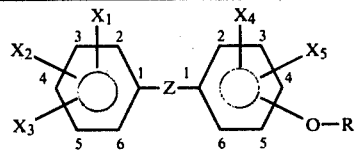

| Example | Code Number | Z | $X_1$ | $X_2$ | $X_3$ | $X_4$ | $X_5$ | Position —O—R | R |
|---|---|---|---|---|---|---|---|---|---|
| 1 | 163 | CO | 4-$NO_2$ | H | H | H | H | para | β-D-Xyl |
| 2 | 459 | CO | 3-$NO_2$ | H | H | H | H | para | β-D-Xyl |
| 3 | 171 | CO | 4-Cl | H | H | H | H | para | β-D-Xyl |
| 4 | 433 | CO | 4-Br | H | H | H | H | para | β-D-Xyl |
| 5 | 456 | CO | 2-Cl | H | H | H | H | para | β-D-Xyl |
| 6 | 511 | CO | 2-$NO_2$ | H | H | H | H | para | β-D-Xyl |
| 7 | 554 | CO | 2-$NH_2$ | H | H | H | H | para | β-D-Xyl |
| 8 | 193 | CO | 4-$NH_2$ | H | H | H | H | para | β-D-Xyl |
| 9 | 466 | CO | 3-$NH_2$ | H | H | H | H | para | β-D-Xyl |
| 10 | 676 | CO | 4-$N(CH_3)_2$ | H | H | H | H | para | β-D-Xyl |
| 11 | 227 | CO | 4-$CF_3$ | H | H | H | H | para | β-D-Xyl |
| 12 | 229 | CO | 4-$CH_3$ | H | H | H | H | para | β-D-Xyl |
| 13 | 465 | CO | 3-$CF_3$ | H | H | H | H | para | β-D-Xyl |
| 14 | 435 | CO | 2-$CH_3$ | H | H | H | H | para | β-D-Xyl |
| 15 | — | CO | 2-$OCH_3$ | H | H | H | H | para | β-D-Xyl |
| 16 | 476 | CO | 3-$OCH_3$ | H | H | H | H | para | β-D-Xyl |
| 17 | 486 | CO | 4-$OCH_3$ | H | H | H | H | para | β-D-Xyl |
| 18 | 262 | CO | H | H | H | H | H | para | β-D-Xyl |
| 19 | 228 | CO | 4-$NO_2$ | H | H | H | H | para | β-D-Glu |
| 20 | 264 | CO | 4-$NO_2$ | H | H | H | H | para | β-D-Gal |
| 21 | 243 | CO | 2-$CH_3$ | H | H | 3-$CH_3$ | 5-$CH_3$ | para | β-D-Xyl |
| 22 | 560 | CO | 4-Cl | H | H | 3-$CH_3$ | 5-$CH_3$ | para | β-D-Xyl |
| 23 | 487 | CO | 4-$NO_2$ | H | H | 3-$CH_3$ | 5-$CH_3$ | para | β-D-Xyl |
| 24 | — | CO | 4-$NH_2$ | H | H | 3-$CH_3$ | 5-$CH_3$ | para | β-D-Xyl |
| 25 | 241 | CO | H | H | H | 3-$NO_2$ | 5-$CH_3$ | para | β-D-Xyl |
| 26 | 242 | CO | 2-$CH_3$ | H | H | 3-$CH_3$ | 5-$CH_3$ | para | β-D-Glu—NHAc |
| 27 | 357 | CO | 4-OH | 2$CH_3$ | H | 3-$CH_3$ | 5-$CH_3$ | para | β-D-Glu |
| 28 | 572 | CO | 4-Cl | H | H | 3-$CH_3$ | H | para | β-D-Xyl |
| 29 | 457 | CO | 4-$NO_2$ | H | H | 3-$CH_3$ | H | para | β-D-Xyl |
| 30 | — | CO | 4-$NH_2$ | H | H | 3-$CH_3$ | H | para | β-D-Xyl |
| 31 | 431 | CO | 2-Cl | 4-Cl | H | H | H | para | β-D-Xyl |
| 32 | 462 | CO | 2-$CH_3$ | 4-$CH_3$ | 6-$CH_3$ | H | H | para | β-D-Xyl |
| 33 | 510 | CO | 3-$OCH_3$ | 4-$OCH_3$ | 5-$OCH_3$ | H | H | para | β-D-Xyl |
| 34 | 652 | CO | 2-$CH_3$ | 4-$CH_3$ | 6-$CH_3$ | 3-$CH_3$ | 5-$CH_3$ | para | β-D-Xyl |
| 35 | — | CO | 4-$NO_2$ | 2-$CH_3$ | H | 3-$CH_3$ | 5-$CH_3$ | para | β-D-Xyl |
| 36 | — | CO | 4-$NH_2$ | 2-$CH_3$ | H | 3-$CH_3$ | 5-$CH_3$ | para | β-D-Xyl |
| 37 | 397 | CO | 2-$CH_3$ | 6-$CH_3$ | H | 3-$CH_3$ | 5-$CH_3$ | para | β-D-Glu—NHAc |
| 38 | — | CO | 4-$NH_2$ | H | H | H | H | para | β-D-Glu—NHAc |
| 39 | — | CO | 4-$NH_2$ | H | H | H | H | para | β-D-Glu |
| 40 | — | CO | 4-$NH_2$ | H | H | H | H | para | β-D-Gal |
| 41 | 236 | CO | 4-$NO_2$ | H | H | H | H | para | $(QAc)_3$—β-D-Xyl |
| 42 | 260 | CO | 4-NCS | H | H | H | H | para | $(QAc)_3$—β-D-Xyl |
| 43 | 172 | CO | 4-Cl | H | H | H | H | para | β-D-Glu—NHAc |
| 44 | 207 | CO | 4-$NO_2$ | H | H | H | H | para | β-D-Glu—NHAc |
| 45 | 430 | CO | H | H | H | H | H | meta | β-D-Xyl |
| 46 | 650 | CO | 4-$NO_2$ | H | H | H | H | meta | β-D-Xyl |
| 47 | — | CO | 4-$NH_2$ | H | H | H | H | meta | β-D-Xyl |
| 48 | 427 | CO | 4-Cl | H | H | H | H | meta | β-D-Xyl |
| 49 | 432 | CO | 4-$CH_3$ | H | H | H | H | meta | β-D-Xyl |
| 50 | — | CO | 4-$CH_3$ | H | H | 4-$CH_3$ | H | meta | β-D-Xyl |
| 51 | — | CO | 3-$CF_3$ | H | H | H | H | meta | β-D-Xyl |
| 52 | 434 | CO | 2-$CH_3$ | H | H | H | H | meta | β-D-Xyl |
| 53 | 428 | CO | 4-$CF_3$ | H | H | H | H | meta | β-D-Xyl |
| 54 | 429 | CO | 4-$OCH_3$ | H | H | H | H | meta | β-D-Xyl |
| 55 | — | CO | H | H | H | H | H | ortho | β-D-Xyl |

TABLE I-continued

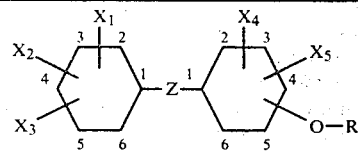

| Example | Code Number | Z | X₁ | X₂ | X₃ | X₄ | X₅ | Position —O—R | R |
|---|---|---|---|---|---|---|---|---|---|
| 56 | — | CO | 4-Cl | H | H | H | H | ortho | β-D-Xyl |
| 57 | — | CO | 4-NO₂ | H | H | H | H | ortho | β-D-Xyl |
| 58 | — | CO | 4-NH₂ | H | H | H | H | ortho | β-D-Xyl |
| 59 | — | CO | 2-CH₃ | H | H | 5-Cl | H | ortho | β-D-Xyl |
| 60 | 677 | CO | 2-CH₃ | H | H | 5-CH₃ | H | ortho | β-D-Xyl |
| 61 | — | CO | 4-NO₂ | H | H | 5-CH₃ | H | ortho | β-D-Xyl |
| 62 | — | CO | 4-NH₂ | H | H | 5-CH₃ | H | ortho | β-D-Xyl |
| 63 | — | CO | 4-NO₂ | H | H | 5-Cl | H | ortho | β-D-Xyl |
| 64 | — | CO | 4-NH₂ | H | H | 5-Cl | H | ortho | β-D-Xyl |
| 65 | 222 | CO | 4-NHC(=S)—OCH₃ | H | H | H | H | para | β-D-Xyl |
| 66 | 289 | CO | 4-OC(CH₃)₂—CO₂—CH(CH₃)₂ | H | H | H | H | para | β-D-Xyl |
| 67 | 358 | CO | 4-Cl | H | H | H | H | para | (SO₃NH₄)₃—β-D-Glu—NHAc |
| 68 | 416 | CO | 2-CH₃ | H | H | 3-CH₃ | 5-CH₃ | para | (SO₃NH₄)₃—β-D-Glu—NHAc |
| 69 | 488 | CO | 2-CH₃ | H | H | H | H | para | (OAc)₃—β-D-Xyl |
| 70 | 490 | CO | 2-Cl | H | H | H | H | para | (QAc)₃—β-D-Xyl |
| 71 | 497 | CO | 2-CH₃ | 4-CH₃ | 6-CH₃ | H | H | meta | β-D-Xyl |
| 72 | 498 | CO | 3-NO₂ | H | H | H | H | para | (OSO₃Na)₃—β-D-Xyl, 3H₂O |
| 73 | 499 | CO | 2-CH₃ | 4-CH₃ | 6-CH₃ | H | H | para | (OAc)₃—β-D-Xyl |
| 74 | 500 | CO | 2-Cl | 4-Cl | H | H | H | para | (OAc)₃—β-D-Xyl |
| 75 | 501 | CO | 4-Br | H | H | H | H | para | (OAc)₃—β-D-Xyl |
| 76 | 502 | CO | 4-CH₃ | H | H | H | H | para | (OAc)₃—β-D-Xyl |
| 77 | 503 | CO | 4-NH₂ | H | H | H | H | para | (OAc)₃—β-D-Xyl |
| 78 | 518 | CO | 2-NO₂ | H | H | H | H | para | (OAc)₃—β-D-Xyl |
| 79 | 519 | CO | 3-OCH₃ | 4-OCH₃ | 5-OCH₃ | H | H | para | (OAc)₃—β-D-Xyl |
| 80 | 520 | CO | 3-NO₂ | H | H | H | H | para | (OAc)₃—β-D-Xyl |
| 81 | 521 | CO | 4-OCH₃ | H | H | H | H | para | (OAc)₃—β-D-Xyl |
| 82 | 522 | CO | 4-Cl | H | H | H | H | meta | (OAc)₃—β-D-Xyl |
| 83 | 523 | CO | H | H | H | H | H | meta | (OAc)₃—β-D-Xyl |
| 84 | 525 | CO | 3-OCH₃ | 4-OH | 5-OCH₃ | H | H | para | (OAc)₃—β-D-Xyl |
| 85 | 477 | CO | 2-CH₃ | H | H | 3-CH₃ | H | para | β-D-Xyl |
| 86 | 512 | CHOH | 2-Cl | 4-Cl | H | H | H | para | β-D-Xyl |
| 87 | 513 | CHOH | 3-NO₂ | H | H | H | H | para | β-D-Xyl |
| 88 | 514 | CHOH | 2-Cl | H | H | H | H | para | β-D-Xyl |
| 89 | 515 | CHOH | 2-CH₃ | H | H | H | H | para | β-D-Xyl |
| 90 | 516 | CHOH | 4-CH₃ | H | H | H | H | para | β-D-Xyl |
| 91 | 517 | CHOH | 4-Cl | H | H | H | H | para | β-D-Xyl |
| 92 | 526 | CHOH | H | H | H | H | H | para | β-D-Xyl |
| 93 | 527 | CHOH | 3-CF₃ | H | H | H | H | para | β-D-Xyl |
| 94 | 528 | CHOH | 4-Cl | H | H | H | H | para | β-D-Xyl |
| 95 | 529 | CHOH | 4-Br | H | H | H | H | para | β-D-Xyl |
| 96 | 559 | CHOH | 4-NO₂ | H | H | H | H | para | (OAc)₃—β-D-Xyl |
| 97 (a) | 265 | CHOH | 4-NO₂ | H | H | H | H | para | β-D-Xyl |
| 98 (b) | 390 | CHOH | 4-NO₂ | H | H | H | H | para | β-D-Xyl |
| 99 (c) | 391 | CHOH | 4-NO₂ | H | H | H | H | para | β-D-Xyl |
| 100 | 411 | CHOH | 4-Cl | H | H | H | H | para | β-D-Glu—NHAc |
| 101 | 555 | CHOH | 2-NO₂ | H | H | H | H | para | β-D-Xyl |
| 102 | 551 | CO | 2-Cl | H | H | 3-CH₃ | 5-CH₃ | para | β-D-Xyl |
| 103 | 550 | CO | 2-CH₃ | H | H | 3-CH₃ | H | para | (OAc)₃—β-D-Xyl |
| 104 | 549 | CO | 4-NO₂ | H | H | 3-CH₃ | H | para | (OAc)₃—β-D-Xyl |
| 105 | 558 | CHOH | 2-CH₃ | H | H | 3-CH₃ | H | para | β-D-Xyl |
| 106 (d) | 557 | CHOH | 4-CH₃ | H | H | H | H | meta | β-D-Xyl |
| 107 (d) | 556 | CHOH | 4-CH₃ | H | H | H | H | meta | β-D-Xyl |
| 108 | 541 | CO | 3-CF₃ | H | H | H | H | para | (OAc)₃—β-D-Xyl |
| 109 | 561 | CO | 4-NO₂ | H | H | H | H | para | (OAc)₃—β-DGluNHac |
| 110 | 562 | CO | 4-NO₂ | H | H | H | H | para | (OAc)₄—β-DGlu |
| 111 | 563 | CO | 4-CH₃ | H | H | H | H | para | βDGlu NHAc |
| 112 | 564 | CO | 4-CH₃ | H | H | H | H | para | (OAc)₃βDGlu NHAc |
| 113 | 565 | CO | 2-Cl | H | H | 3-CH₃ | 5-CH₃ | para | (OAc)₃βD Xyl |
| 114 | 566 | CO | 4-Cl | H | H | 3-CH₃ | 5-CH₃ | para | (OAc)₃βD Xyl |
| 115 | 662 | CHOH | 4-NO₂ | H | H | H | H | para | β-D-Gal |
| 116 | 568 | CO | 4-N(CH₃)₂ | H | H | H | H | para | (OAc)₃βD Xyl |

TABLE I-continued

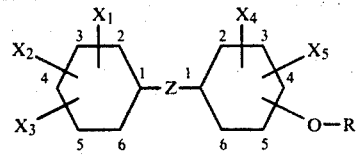

| Example | Code Number | Z | $X_1$ | $X_2$ | $X_3$ | $X_4$ | $X_5$ | Position —O—R | R |
|---|---|---|---|---|---|---|---|---|---|
| 117 | 570 | CHOH | H | H | H | H | H | meta | β-D Xyl |
| 118 | 573 | CO | 4-CF₃ | H | H | H | H | para | β-D-Glu—NHAc |
| 119 | 574 | CO | 4-NO₂ | H | H | 3-CH₃ | 5-CH₃ | para | β-D-Glu—NHAc |
| 120 | 575 | CO | 2-Cl | H | H | H | H | para | β-D-Glu—NHAc |
| 121 | 576 | CO | 2-CH₃ | H | H | H | H | para | β-D-Glu—NHAc |
| 122 | 583 | CO | 2-CH₃ | H | H | 3-CH₃ | H | para | β-D-Glu—NHAc |
| 123 | 589 | CHOH | 4-NO₂ | H | H | H | H | para | β-D-Glu—NHAc |
| 124 | 590 | CO | 4-Cl | H | H | H | H | para | β-D-Glu |
| 125 | 591 | CO | 2-OH | H | H | H | H | para | β-D-Xyl |
| 126 | 602 | CO | H | H | H | H | H | para | β-D-Glu |
| 127 | 605 | CO | 4-CH₃ | H | H | H | H | para | β-D-Glu |
| 128 | 618 | CHOH | 4-CH₃ | H | H | H | H | para | β-D-Glu NHAc |
| 129 | 619 | CHOH | 4-NO₂ | H | H | H | H | para | β-D-Glu |
| 130 | 620 | CO | N | H | H | H | H | para | β-D-Glu NHAc |
| 131 | 621 | CHOH | 4Cl | H | H | H | H | para | β-D-Glu |
| 132 | 680 | CO | 3-CF₃ | H | H | H | H | meta | β-D-Xyl |
| 133 | 651 | CHOH | 4CH₃ | H | H | H | H | para | β-D-Glu |
| 134 | 653 | CHOH | H | H | H | H | H | para | β-D-Glu |
| 135 | 679 | CO | 4-CH₃ | H | H | 4-CH₃ | H | meta | β-D-Xyl |
| 136 | 678 | CHOH | 4-NO₂ | H | H | H | H | ortho | β-D-Xyl |
| 137 | — | CO | 4-Cl | H | H | H | H | para | β-D-Gal |
| 138 | — | CHOH | 4-NH₂ | H | H | H | H | para | β-D-Gal |
| 139 | — | CO | 4-NO₂ | H | H | H | H | para | α-L-Rham |
| 140 | — | CO | H | H | H | 2-CH₃ | H | para | β-D-Xyl |
| 141 | — | CO | 4-NO₂ | H | H | H | H | ortho | (OAc)₃—β-D-Xyl |

Notes:
(a) mixture of the two diastereoisomers
(b) dextrogyre diastereoisomer
(c) laevogyre diastereoisomer
(d) Example compounds 106 and 107 are diastereoisomers (see optical rotation values in Table II)

TABLE II

| | | PHYSICAL PROPERTIES | | | |
|---|---|---|---|---|---|
| | | Melting Point | OPTICAL ROTATION | | |
| Example | Code Number | (°C.) | $\alpha_D^{20°C.}$ | Concentration | Solvent |
| 1 | 163 | 200 | −26.6 | 0.6 | MeOH |
| 2 | 459 | 135 | −30 | 0.15 | MeOH |
| 3 | 171 | 174 | −27.04 | 1.054 | MeOH |
| 4 | 433 | 182 | −23.8 | 0.84 | MeOH |
| 5 | 456 | 90 | −21 | 0.7 | MeOH |
| 6 | 511 | 130 | −23 | 0.5 | MeOH |
| 8 | 193 | 200 | −26.5 | 0.49 | MeOH |
| 9 | 466 | 150 | −26 | 0.3 | MeOH |
| 10 | 676 | 205 | −47 | 0.5 | MeOH |
| 11 | 227 | 160 | −25.4 | 0.61 | MeOH |
| 12 | 229 | 162 | −26.7 | 0.6 | MeOH |
| 13 | 465 | 100 | −26 | 0.35 | MeOH |
| 14 | 435 | 125 | −21 | 0.5 | MeOH |
| 15 | — | 126 | −6.8 | 0.5 | MeOH |
| 16 | 476 | 154 | −30 | 0.5 | MeOH |
| 17 | 486 | 180 | −26 | 0.5 | MeOH |
| 18 | 262 | 140 | −20 | 0.7 | AcOEt |
| 19 | 228 | 196 | −54.2 | 0.6 | MeOH |
| 20 | 264 | 220 | −39.34 | 0.61 | Pyridine |
| 21 | 243 | 132 | +17.25 | 0.58 | MeOH |
| 22 | 560 | 188 | +32 | 0.5 | MeOH |
| 23 | 487 | 185 | +13 | 0.25 | MeOH |
| 25 | 241 | 100 | −83.3 | 0.63 | MeOH |
| 26 | 242 | >265 | −9.4 | 0.6 | Pyridine |
| 27 | 357 | 222 | −12.8 | 0.7 | Pyridine |
| 29 | 457 | 200 | −27 | 0.2 | MeOH |
| 31 | 431 | 172 | −21.5 | 0.72 | MeOH |
| 32 | 462 | 130 | −24 | 0.5 | MeOH |
| 33 | 510 | 170 | −22 | 0.5 | MeOH |
| 37 | 397 | 220 | +17 | 0.2 | MeOH |
| 41 | 236 | 150 | −33.3 | 0.9 | ClCH₂CH₂Cl |
| 42 | 260 | 143 | — | — | — |
| 43 | 172 | 240 | −8.8 | 0.91 | Pyridine |
| 44 | 207 | 206 | +12.5 | 0.6 | MeOH |

TABLE II-continued

PHYSICAL PROPERTIES

| Example | Code Number | Melting Point (°C.) | $\alpha_D^{20°C}$ | Concentration | Solvent |
|---|---|---|---|---|---|
| | | | OPTICAL ROTATION | | |
| 45 | 430 | 140 | −30 | 0.5 | MeOH |
| 46 | 650 | 108 | −29.6 | 0.5 | MeOH |
| 48 | 427 | 80 | −25.5 | 0.7 | MeOH |
| 49 | 432 | 154 | −28.6 | 0.77 | MeOH |
| 52 | 434 | 168 | −32.5 | 0.8 | MeOH |
| 53 | 428 | 120 | −38 | 0.5 | MeOH |
| 54 | 429 | 140 | −27 | 0.7 | MeOH |
| 56 | — | 129.5 | — | — | — |
| 57 | — | 164 | — | — | — |
| 60 | 677 | 187 | −68 | 0.6 | acetone |
| 66 | 289 | 144 | −22.13 | 0.61 | MeOH |
| 67 | 358 | 200 (with decomposition) | −2.1 | 2.6 | H$_2$O |
| 68 | 416 | >265 | +11 | 1 | H$_2$O |
| 69 | 488 | 115 | −22 | 0.52 | MeOH |
| 70 | 490 | 165 | −24 | 0.5 | MeOH |
| 71 | 497 | 220 | −33 | 0.5 | MeOH |
| 72 | 498 | — | −40 | 0.2 | MeOH |
| 73 | 499 | 153 | −45 | 0.5 | MeOH |
| 74 | 500 | 140 | −20 | 0.5 | MeOH |
| 75 | 501 | 150 | −12 | 0.5 | MeOH |
| 76 | 502 | 138 | −22 | 0.5 | MeOH |
| 77 | 503 | 170 | −17 | 0.5 | MeOH |
| 78 | 518 | 145 | −25 | 0.5 | MeOH |
| 79 | 519 | 114 | −16 | 0.5 | MeOH |
| 80 | 520 | 145 | −26 | 0.5 | MeOH |
| 81 | 521 | 144 | −21 | 0.5 | MeOH |
| 82 | 522 | 126 | −26 | 0.5 | MeOH |
| 83 | 523 | 148 | −28 | 0.5 | MeOH |
| 84 | 525 | 162 | −48 | 0.5 | MeOH |
| 85 | 477 | 135 | −25 | 0.5 | MeOH |
| 86 | 512 | 152 | −16.7 | 0.54 | MeOH |
| 87 | 513 | 125 | −15 | 0.5 | MeOH |
| 88 | 514 | 210 | −23 | 0.5 | MeOH |
| 89 | 515 | 210 | −26 | 0.5 | MeOH |
| 90 | 516 | 206 | −24 | 0.5 | MeOH |
| 91 | 517 | 185 | −16 | 0.5 | MeOH |
| 92 | 526 | 190 | −26 | 0.5 | MeOH |
| 93 | 527 | 168 | −20 | 0.5 | MeOH |
| 94 | 528 | 84 | −37 | 0.5 | MeOH |
| 95 | 529 | 190 | −23 | 0.5 | MeOH |
| 96 | 559 | 80 | −25 | 0.5 | MeOH |
| 97 | 265 | 142 | −17 | 0.5 | MeOH |
| 98 | 390 | 162 | +21 | 0.48 | MeOH |
| 99 | 391 | 158 | −50 | 0.48 | MeOH |
| 100 | 411 | 218 | +13 | 0.5 | MeOH |
| 101 | 555 | 198 | −45 | 0.5 | MeOH |
| 102 | 551 | 190 | +13 | 0.5 | MeOH |
| 103 | 550 | 102 | −33 | 0.5 | MeOH |
| 104 | 549 | 164 | −46 | 0.5 | CHCl$_3$ |
| 105 | 558 | 110 | −9.5 | 0.42 | MeOH |
| 106 | 557 | 50 | −24 | 0.41 | MeOH |
| 107 | 556 | 50 | −11 | 0.45 | MeOH |
| 108 | 541 | 140 | −27 | 0.5 | MeOH |
| 109 | 561 | 240 | −64 | 0.50 | CHCl$_3$ |
| 110 | 562 | 218 | — | — | — |
| 111 | 563 | 212 | +25 | 0.20 | EtOH |
| 112 | 564 | 220 | −12.7 | 0.55 | CHCl$_3$ |
| 113 | 565 | 130 | −8 | 0.50 | CHCl$_3$ |
| 114 | 506 | 150 | +40 | 0.50 | CHCl$_3$ |
| 115 | 662 | 172 | — | — | — |
| 116 | 568 | 152 | — | — | — |
| 117 | 570 | 180 | −2.3 | 0.44 | MeOH |
| 118 | 573 | 238 | +20 | 0.40 | MeOH |
| 119 | 574 | 268 | — | — | — |
| 120 | 575 | 226 | +20 | 0.40 | MeOH |
| 121 | 576 | 230 | +22 | 0.50 | MeOH |
| 122 | 583 | 238 | +4 | 0.50 | MeOH |
| 123 | 589 | 215 | +20 | 0.50 | MeOH |
| 124 | 590 | 152 | — | — | — |
| 125 | 591 | 180 | −60 | 0.40 | MeOH |
| 126 | 602 | 163 | −54 | 0.5 | MeOH |
| 127 | 605 | 110 | −55 | 0.48 | MeOH |
| 128 | 618 | 210 | +72 | 0.2 | EtOH—H$_2$O (4:1)v/v |
| 129 | 619 | 140 | −66 | 0.5 | MeOH |
| 130 | 620 | 250 | +20 | 0.5 | MeOH |
| 131 | 621 | 130 | −64 | 0.5 | MeOH |
| 132 | | 135 | −66 | 0.5 | MeOH |
| 133 | 651 | 84 | −26.4 | 0.72 | MeOH |

TABLE II-continued

PHYSICAL PROPERTIES

| Example | Code Number | Melting Point (°C.) | $\alpha_D^{20°C}$ | Concentration | Solvent |
|---|---|---|---|---|---|
| 134 | 653 | 90 | −43.8 | 0.48 | MeOH |
| 135 | 679 | 125 | −66 | 0.6 | MeOH |
| 136 | 678 | 207 | — | — | — |
| 137 | — | 202 | — | — | — |
| 138 | — | Decomposition at 60° C. | — | — | — |
| 139 | — | 94 | — | — | — |
| 140 | — | 110 | −61 | 0.3 | MeOH |
| 141 | — | 142 | — | — | — |

TABLE III

Acute toxicity in mice per I.P. route

| Example | Code Number | DL-0; DL-50 mg/kg IP |
|---|---|---|
| 1 | 163 | DL-0 > 800 |
| 2 | 459 | DL-0 > 800 |
| 3 | 171 | DL-0 > 800 |
| 4 | 433 | DL-0 > 800 |
| 5 | 456 | DL-0 > 800 |
| 6 | 511 | DL-50 = 600 |
| 7 | 554 | DL-0 > 800 |
| 8 | 193 | DL-0 > 800 |
| 11 | 227 | DL-0 > 800 |
| 12 | 229 | DL-0 > 800 |
| 13 | 465 | DL-50 = 170 |
| 14 | 435 | DL-50 = 740 |
| 16 | 476 | DL-0 > 800 |
| 17 | 486 | DL-50 = 1600 |
| 18 | 262 | DL-50 > 1000 |
| 19 | 228 | DL-0 > 800 |
| 20 | 264 | DL-0 > 800 |
| 21 | 243 | DL-50 = 600 |
| 22 | 560 | DL-50 = 500 |
| 23 | 487 | DL-50 = 750 |
| 25 | 241 | DL-50 = 330 |
| 26 | 242 | DL-50 = 700 |
| 27 | 357 | DL-0 > 800 |
| 28 | 572 | DL-0 > 800 |
| 29 | 457 | DL-0 > 800 |
| 31 | 431 | DL-0 > 800 |
| 32 | 462 | DL-0 > 800 |
| 33 | 510 | DL-0 > 800 |
| 37 | 397 | DL-50 = 600 |
| 41 | 236 | DL-0 > 800 |
| 42 | 260 | DL-0 > 800 |
| 43 | 172 | DL-0 > 800 |
| 44 | 207 | DL-0 > 800 |
| 45 | 430 | DL-0 > 800 |
| 48 | 427 | DL-50 = 220 |
| 49 | 432 | DL-0 > 800 |
| 52 | 434 | DL-0 > 800 |
| 53 | 428 | DL-50 = 550 |
| 54 | 429 | DL-0 > 800 |
| 65 | 222 | DL-0 > 800 |
| 67 | 358 | DL-0 > 800 |
| 68 | 416 | DL-0 > 800 |
| 69 | 488 | DL-50 = 900 |
| 70 | 490 | DL-0 > 800 |
| 71 | 497 | DL-0 > 800 |
| 72 | 498 | DL-50 = 650 |
| 73 | 499 | DL-0 > 800 |
| 74 | 500 | DL-0 > 800 |
| 75 | 501 | DL-0 > 800 |
| 76 | 502 | DL-0 > 800 |
| 77 | 503 | DL-0 > 800 |
| 78 | 518 | DL-0 > 800 |
| 79 | 519 | DL-0 > 800 |
| 80 | 520 | DL-0 > 800 |
| 81 | 521 | DL-0 > 800 |
| 82 | 522 | DL-0 > 800 |
| 83 | 523 | DL-0 > 800 |
| 84 | 525 | DL-0 > 800 |
| 85 | 477 | DL-50 > 550 |
| 86 | 512 | DL-50 > 350 |
| 87 | 513 | DL-50 > 600 |
| 88 | 514 | DL-0 > 800 |
| 89 | 515 | DL-0 > 800 |
| 90 | 516 | DL-0 > 800 |
| 91 | 517 | DL-0 > 800 |
| 92 | 526 | DL-50 = 1400 |
| 93 | 527 | DL-0 > 800 |
| 94 | 528 | DL-50 = 330 |
| 95 | 529 | DL-0 > 800 |
| 97 | 265 | DL-50 > 1000 |
| 100 | 411 | DL-0 > 800 |
| 101 | 555 | DL-0 > 800 |
| 102 | 551 | DL-0 > 800 |
| 103 | 550 | DL-0 > 800 |
| 104 | 549 | DL-0 > 800 |
| 105 | 558 | DL-50 = 450 |
| 106 | 557 | DL-50 = 500 |
| 107 | 556 | DL-50 = 550 |
| 108 | 541 | DL-0 > 800 |
| 109 | 561 | DL-0 > 800 |
| 110 | 562 | DL-0 > 800 |
| 111 | 563 | DL-50 = 750 |
| 112 | 564 | DL-0 > 800 |
| 113 | 565 | DL-50 = 630 |
| 114 | 566 | DL-0 > 800 |
| 116 | 568 | DL-0 > 800 |
| 117 | 570 | DL-50 = 1000 |
| 118 | 573 | DL-0 > 800 |
| 119 | 574 | DL-0 > 800 |
| 120 | 575 | DL-0 > 800 |
| 121 | 576 | DL-0 > 800 |
| 122 | 583 | DL-0 > 800 |
| 123 | 589 | DL-0 > 800 |
| 124 | 590 | DL-0 > 800 |
| 125 | 591 | DL-50 = 1700 |
| 126 | 602 | DL-0 > 800 |
| 127 | 605 | DL-50 = 700 |
| 128 | 618 | DL-0 > 800 |
| 129 | 619 | DL-0 > 800 |
| 130 | 620 | DL-0 > 800 |
| 131 | 621 | DL-50 = 730 |

TABLE IV

Anti-ulcer activity

| Example | Code Number | Ulcer index |
|---|---|---|
| 1 | 163 | 0.56 |
| 2 | 459 | 0.84 |
| 4 | 433 | 1.04 |
| 6 | 511 | 0.45 |
| 8 | 193 | 0.25 |
| 11 | 227 | 0 (200 mg/kg P.O.) |
| 12 | 229 | 0.26 |
| 13 | 465 | 0.46 |
| 16 | 476 | 0.73 |
| 17 | 486 | 0.69 |
| 19 | 228 | 0.74 |
| 20 | 264 | 0.62 |
| 21 | 243 | 0.16 |
| 22 | 560 | 1.46 |
| 23 | 487 | 0.52 |

TABLE IV-continued

Anti-ulcer activity

| Example | Code Number | Ulcer index |
|---|---|---|
| 25 | 241 | 0.54 |
| 26 | 242 | 0.60 |
| 27 | 357 | 0.42 |
| 31 | 431 | 1.04 |
| 32 | 462 | 0.54 |
| 33 | 510 | 0.46 |
| 37 | 397 | 1.02 |
| 41 | 236 | 0.40 |
| 43 | 172 | 0.52 |
| 44 | 207 | 0.385 |
| 45 | 430 | 1.11 |
| 48 | 427 | 0.75 |
| 49 | 432 | 1.21 |
| 53 | 428 | 0.64 |
| 54 | 429 | 0.57 |
| 67 | 358 | 0.81 |
| 69 | 488 | 0.78 |
| 70 | 490 | 0.56 |
| 71 | 497 | 0.98 |
| 72 | 498 | 0.47 |
| 73 | 499 | 0.52 |
| 74 | 500 | 0.91 |
| 75 | 501 | 0.32 |
| 76 | 502 | 0.38 |
| 80 | 520 | 1.00 |
| 81 | 521 | 0.64 |
| 86 | 512 | 0.50 |
| 87 | 513 | 0.35 |
| 88 | 514 | 0.39 |
| 89 | 515 | 0.88 |
| 90 | 516 | 0.57 |
| 91 | 517 | 0.72 |
| 95 | 529 | 0.52 |
| 97 | 265 | 0.52 |
| 100 | 411 | 0.35 |
| 101 | 555 | 0.56 |
| 102 | 551 | 0.49 |
| 103 | 550 | 0.65 |
| 104 | 549 | 0.84 |
| 108 | 541 | 0.30 |
| 109 | 561 | 0.65 |
| 110 | 562 | 0.71 |
| 111 | 563 | 0.42 |
| 112 | 564 | 0.68 |
| 116 | 568 | 0.44 |
| 117 | 570 | 0.59 |
| 118 | 573 | 0.53 |
| 119 | 574 | 0.47 |
| 121 | 576 | 0.39 |
| 122 | 583 | 0.91 |

TABLE V

Blood platelet anti-aggregation activity

| Example | Code Number | Inhibition of platelet aggregation (a) |
|---|---|---|
| 1 | 163 | ++ |
| 8 | 193 | ++ |
| 12 | 229 | + |
| 14 | 435 | ++ (75 mg/kg IP) |
| 21 | 243 | ++ |
| 54 | 429 | ++ |
| 67 | 358 | + |
| 79 | 519 | ++ |
| 94 | 529 | + (33 mg/kg IP) |
| 97 | 265 | ++ |
| 102 | 551 | ++ |
| 104 | 549 | ++ |
| 105 | 558 | + (45 mg/kg IP) |
| 113 | 565 | ++ (63 mg/kg IP) |
| 114 | 566 | + |

TABLE V-continued

Blood platelet anti-aggregation activity

| Example | Code Number | Inhibition of platelet aggregation (a) |
|---|---|---|
| 118 | 573 | + |

Note
(a) the inhibition percentage of blood platelet aggregation corresponds to the following notation:
+ inhibition of 25 to 39%
++ inhibition higher than or equal to 40%

TABLE VI

Veinous anti-thrombus activity

| Example | Code Number | Diminution of veinous thrombus (a) |
|---|---|---|
| 2 | 459 | + |
| 3 | 171 | + |
| 4 | 433 | + |
| 5 | 456 | ++ |
| 6 | 511 | + |
| 7 | 554 | ++ |
| 8 | 193 | ++ |
| 14 | 435 | ++ |
| 17 | 486 | + |
| 18 | 262 | + |
| 23 | 487 | + |
| 29 | 457 | + |
| 45 | 430 | + |
| 54 | 429 | + |
| 67 | 358 | + |
| 69 | 488 | + |
| 70 | 490 | + |
| 71 | 497 | + |
| 75 | 501 | + |
| 76 | 502 | + |
| 77 | 503 | + |
| 81 | 521 | + |
| 85 | 477 | ++ |
| 86 | 512 | + |
| 87 | 513 | ++ |
| 88 | 514 | ++ |
| 89 | 515 | ++ |
| 91 | 517 | + |
| 92 | 526 | + |
| 97 | 265 | ++ |
| 98 | 390 | ++ |
| 99 | 391 | + |
| 101 | 555 | ++ |
| 102 | 551 | + |
| 106 | 557 | ++ (50 mg/kg IP) |
| 108 | 541 | + |
| 119 | 574 | ++ |
| 123 | 589 | + |
| 125 | 591 | + |
| 130 | 620 | + |
| 131 | 621 | + |

Note
(a) notation:
+ inhibition of 30 to 49%
++ inhibition higher than or equal to 50%

TABLE VII

Anti-hypoxic activity

| Example | Code Number | Survival (a) |
|---|---|---|
| 1 | 163 | +++ |
| 3 | 171 | +++ |
| 8 | 193 | +++ |
| 11 | 227 | ++ |
| 12 | 229 | ++ |
| 13 | 465 | ++ |
| 16 | 476 | + |
| 19 | 228 | ++ |
| 26 | 242 | + |
| 28 | 572 | ++ |
| 41 | 236 | +++ |
| 43 | 172 | +++ |
| 44 | 207 | +++ |

TABLE VII-continued

| | Anti-hypoxic activity | |
|---|---|---|
| Example | Code Number | Survival (a) |
| 76 | 502 | ++ |
| 83 | 523 | ++ |
| 85 | 477 | + |
| 91 | 517 | +++ |
| 94 | 528 | + |
| 100 | 411 | ++ |
| 101 | 555 | + |
| 102 | 551 | +++ |
| 103 | 550 | ++ |
| 104 | 549 | ++ |
| 108 | 541 | + |
| 109 | 561 | ++ |
| 110 | 562 | ++ |
| 111 | 563 | ++ |
| 112 | 564 | ++ |
| 113 | 565 | +++ |
| 114 | 566 | ++ |
| 116 | 568 | + |
| 117 | 570 | ++ |
| 118 | 573 | ++ |
| 119 | 574 | +++ |
| 120 | 575 | +++ |
| 121 | 576 | + |
| 122 | 583 | + |
| 123 | 589 | ++ |
| 124 | 590 | + |
| 125 | 591 | + |
| 126 | 602 | + |
| 127 | 605 | ++ |
| 128 | 618 | ++ |
| 130 | 620 | ++ |
| 131 | 621 | ++ |

Note
(a) survival percentage to hypoxic aggression is given according to the following notation
+ from 30 to 49%
++ from 50 to 79%
+++ higher than or equal to 80%

What is claimed is:

1. Benzoyl- and α-hydroxybenzyl-phenylglycosides selected from the group consisting of:
(i) compounds corresponding to general formula:

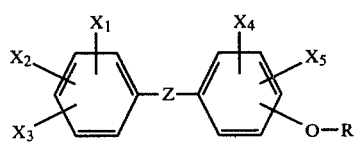

(I)

wherein:
Z represents CO or CHOH;

$X_2$, $X_3$, $X_4$ and $X_5$, which are identical or different, each represent hydrogen, halogen, an alkyl group with 1 to 4 carbon atoms, an alkyl group with 1 to 4 carbon atoms substituted by one or more halogen atoms, an OH group, an alkoxy group with 1 to 4 carbon atoms, an alkoxy group having 1 to 4 carbon atoms substituted by one or more halogen atoms, a nitro group, a cyano group, a thiocyano group, an isothiocyano group, a NR'R" group (where R' and R", which are identical or different, each represent hydrogen or an alkyl group with 1 to 4 carbon atoms);

$X_1$ represents hydrogen, halogen, an alkyl group with 1 to 4 carbon atoms, an alkyl group with 1 to 4 carbon atoms substituted by one or more halogen atoms, an OH group, an alkoxy group with 1 to 4 carbon atoms, an alkoxy group with 1 to 4 carbon atoms substituted by one or more halogen atoms, a nitro group, a cyano group, a thiocyano group, an isothiocyano group, an NR'R" group (where R' and R", which are identical or different, each represent hydrogen or an alkyl group with 1 to 4 carbon atoms), an —NH—CS—O—CH$_3$ group or an —O—C(CH$_3$)$_2$DO$_2$—R''' group (where R''' is an alkyl group with 1 to 4 carbon atoms) and R represents an unsubstituted, non-hydrolyzable monosaccharide carbohydrate radical; or a non-hydrolyzable monosaccharide carbohydrate radical substituted with at least one substituent selected from the group consisting of acyl, alkyl and sulfonyl groups; and (ii) when Z is CHOH, the diastereoisomers of the compounds of (i).

2. A compound according to claim 1, wherein the hydroxyl and amine functions of the group R are acylated, methylated, benzylated or sulfated.

3. A compound according to claim 1, wherein $X_1$, $X_2$, $X_3$, $X_4$ and $X_5$, identical or different, each represent an alkoxy group having 1 to 4 carbon atoms substituted by a radical selected from the group H, Cl, Br, CH$_3$, CF$_3$, OH, OCH$_3$, NO$_2$, NH$_2$, N(CH$_3$)$_2$, and NCS; $X_1$ also representing in para position with respect to the Z group an —OC(CH$_3$)$_2$CO$_2$—CH(CH$_3$)$_2$ or an —NH—CS—OCH$_3$ group when $X_2$, $X_3$, $X_4$, and $X_5$ all represent H; and R represents a non-hydrolyzable, monosaccharide carbohydrate radical selected from the group consisting of β-D-glucosyl, β-D-xylosyl, β-D-galactosyl, and β-D-glucosaminyl, the corresponding carbohydrate radicals in which the hydrogen atom of the OH groups of the carbohydrate radical is replaced by a radical selected from the group consisting of COCH$_3$, CH$_3$, CH$_2$C$_6$H$_5$, SO$_3$HN$_4$, SO$_3$Na, and SO$_3$K, and the corresponding carbohydrate radicals in which the amine function of the carbohydrate radical is substituted by a COCH$_3$ group.

4. [4-(4-nitrobenzoyl)-phenyl]-2,3,4-tri-(O-acetyl)-β-D-xylopyranoside.

5. [4-(4-nitrobenzoyl)-phenyl]-β-D-xylopyranoside.

6. [3-(4-trifluoromethylbenzoyl)-phenyl]-β-D-xylopyranoside.

7. [4-(4-chlorobenzoyl)-phenyl]-3,4,6-tri-(ammonium-sulfate)-2-N-acetyl-β-D-glucosaminide.

8. [4-(4-nitrobenzoyl)-phenyl]-2-N-acetyl-β-D-glucosaminide.

9. [4-(4-nitro-α-hydroxybenzyl)-phenyl]-β-D-xylopyranoside and its diastereoisomers.

10. [4-(4-nitro-α-hydroxybenzyl)-phenyl]-2,3,4-tri-(O-acetyl)-β-D-xylopyranoside.

11. A therapeutic composition containing in association with a physiologically acceptable excipient, an effective ulcer treating amount of a compound according to claim 1.

* * * * *